(12) United States Patent
Finneran et al.

(10) Patent No.: US 9,044,557 B2
(45) Date of Patent: *Jun. 2, 2015

(54) TRACHEAL TUBE SENSOR DISPOSED ON PERMEABLE MEMBRANE

(71) Applicant: Covidien LP, Mansfield, MA (US)

(72) Inventors: Alan Finneran, Offaly (IE); Garret Coady, Dublin (IE); John Desmond, Kildare (IE); Mark Cleary, Dublin (IE); David Powell, Dublin (IE); Patrick Dowling, Kildare (IE)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,635

(22) Filed: Oct. 1, 2013

(65) Prior Publication Data

US 2014/0031656 A1 Jan. 30, 2014

Related U.S. Application Data

(63) Continuation of application No. 12/726,210, filed on Mar. 17, 2010, now Pat. No. 8,568,316.

(51) Int. Cl.
*A61B 5/00* (2006.01)
*A61M 16/00* (2006.01)
(Continued)

(52) U.S. Cl.
CPC ........ *A61M 16/0051* (2013.01); *A61B 5/14503* (2013.01); *A61B 5/14539* (2013.01); *A61B 5/14542* (2013.01); *A61B 5/1459* (2013.01); *A61B 5/1473* (2013.01); *A61B 5/6853* (2013.01); *A61B 5/6885* (2013.01); *A61M 16/04* (2013.01); *A61M 2205/3523* (2013.01); *A61M 2230/202* (2013.01); *A61M 2230/205* (2013.01); *A61M 2230/208* (2013.01); *A61B 5/0002* (2013.01); *A61B 5/0071* (2013.01); *A61B 5/0075* (2013.01); *A61B 5/0833* (2013.01); *A61B 5/0836* (2013.01); *A61B 5/742* (2013.01);
(Continued)

(58) Field of Classification Search
None
See application file for complete search history.

(56) References Cited

U.S. PATENT DOCUMENTS 4,886,059 A 12/1989 Weber
4,966,141 A 10/1990 Bacaner et al.
(Continued)

FOREIGN PATENT DOCUMENTS

WO 9710495 A1 3/1997
WO 0048510 A1 8/2000

OTHER PUBLICATIONS

International Search Report and Written Opinion for PCT Application No. PCT/US2011/028128 dated Sep. 26, 2011; 15 pgs.
(Continued)

*Primary Examiner* — Etsub Berhanu
(74) *Attorney, Agent, or Firm* — Fletcher Yoder PC (57) ABSTRACT

Various embodiments of a tracheal tube having a sensor coupled to a selectively permeable membrane are provided. In some embodiments, the membrane may be permeable to one or more blood gases and/or blood analytes. Certain embodiments of the endotracheal tube may be capable of deploying the sensor during intubation to sense one or more indicators of blood flow characteristics, such as a level of blood gases and/or blood analytes, in the respiratory tract. Embodiments of the present invention may include positioning of the sensor in a variety of suitable positions with respect to the permeable membrane, such as mounting the sensor to the underside of an inflatable permeable membrane.

15 Claims, 6 Drawing Sheets

(51) Int. Cl.
  *A61B 5/145*    (2006.01)
  *A61B 5/1473*   (2006.01)
  *A61M 16/04*    (2006.01)
  *A61B 5/083*    (2006.01)
  *A61B 5/1459*   (2006.01)

(52) U.S. Cl.
  CPC ....... *A61M 16/0057* (2013.01); *A61M 16/0434* (2013.01)

(56) References Cited

U.S. PATENT DOCUMENTS

| | | | |
|---|---|---|---|
| 5,076,268 A | 12/1991 | Weber | |
| 5,408,999 A | 4/1995 | Singh et al. | |
| 5,579,763 A | 12/1996 | Weil et al. | |
| 6,055,447 A | 4/2000 | Weil et al. | |
| 6,071,237 A | 6/2000 | Weil et al. | |
| 6,216,024 B1 | 4/2001 | Weil et al. | |
| 6,258,046 B1 | 7/2001 | Kimball et al. | |
| 6,815,211 B1 | 11/2004 | Blazewicz et al. | |
| 6,843,250 B2 | 1/2005 | Efrati | |
| 6,955,651 B2 | 10/2005 | Kuck et al. | |
| 6,961,600 B2 | 11/2005 | Kohl et al. | |
| 7,273,050 B2 | 9/2007 | Wei | |
| 2002/0115936 A1 | 8/2002 | Koblanski | |
| 2003/0220551 A1 | 11/2003 | Kimball et al. | |
| 2004/0127800 A1 | 7/2004 | Kimball et al. | |
| 2004/0221853 A1 | 11/2004 | Miller | |
| 2005/0279360 A1 | 12/2005 | Wei | |
| 2007/0093702 A1 | 4/2007 | Yu et al. | |
| 2008/0210235 A1 | 9/2008 | Field et al. | |
| 2009/0038620 A1 | 2/2009 | Efrati | |
| 2011/0230742 A1* | 9/2011 | Finneran et al. | 600/364 |

OTHER PUBLICATIONS

Cardos, et al., "Portable devices used to detect endotracheal intubation during emergency situations: a Review", Critical Care Medicine—vol. 26, Issue 5 (May 1988), pp. 957-964.

* cited by examiner

TRACHEAL TUBE SENSOR DISPOSED ON PERMEABLE MEMBRANE

CROSS-REFERENCE TO RELATED APPLICATIONS

This application is a continuation of application Ser. No. 12/726,210, filed Mar. 17, 2010, entitled "Tracheal Tube Sensor Disposed on Permeable Membrane" in the name of Alan Finneran et al.

BACKGROUND

The present disclosure relates generally to medical devices and, more particularly, to airway devices, such as tracheal tubes.

This section is intended to introduce the reader to various aspects of art that may be related to various aspects of the present disclosure, which are described and claimed below. This discussion is believed to be helpful in providing the reader with background information to facilitate a better understanding of the various aspects of the present disclosure. Accordingly, it should be understood that these statements are to be read in this light, and not as admissions of prior art.

Tracheal tubes are often placed in the airway of a patient in medical situations that necessitate protection of the airway from possible obstruction or occlusion. For instance, tracheal tubes may be used in emergency situations, such as when a patient experiences cardiac or respiratory arrest. The underlying condition that necessitates intubation of the patient may also cause a drop in aortic pressure, leading to low blood flow to non-critical organs, such as the respiratory tract, to compensate for an increased need for blood flow to critical organs, such as the brain. A decrease in blood flow to the respiratory tract may be detected by assessing the level of blood gases and/or blood analytes present in the tracheal mucosa.

Some traditional systems measure the level of blood gases and/or blood analytes in the respiratory tract by introducing a sensor into the trachea and contacting the tracheal mucosa. However, critically ill patients ate already intubated with a tracheal tube, and an introduction of an additional sensing device can be uncomfortable and burdensome. Accordingly, systems that deploy the sensor from the tracheal tube already in place in the respiratory tract have been developed. However, such systems often fall short of expectations since they may compromise one or more of the functions of the tracheal tube. For example, some traditional systems may compromise the sealing properties of the cuff coupled to the tracheal tube. Accordingly, there exists a need for improved systems that measure blood gases and/or blood analytes in the respiratory tract without interrupting the proper functioning of the tracheal tube.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of an endotracheal tube (ETT) assembly having a sensor coupled to a selectively permeable membrane are provided. The membrane may be permeable to one or more blood gases and/or blood analytes, and the sensor is configured to measure a presence or amount of at least one blood gas and/or blood analyte, such as carbon dioxide, oxygen, or pH, in the trachea during deployment. The ETT may also include a lumen that is adapted to receive one or more conductors or support cables that facilitate a bidirectional exchange of data, power, and so forth between the sensor and an external support system. The tracheal tube may be disposable rather than reusable, capable of sensing one or more blood gases and/or blood analytes, capable of conveying gas to and from a patient, and capable of deploying one or more sensors during intubation. Embodiments of the disclosed ETT may be used to indirectly monitor the cardiac state of a patient by directly monitoring the level of blood gases and/or blood analytes in the respiratory tract. That is, measurements of such gas and analyte levels in the trachea may be used to determine parameters relating to cardiac output, such as blood flow, and may provide insight into possible cardiac pathologies, such as perfusion failure.

Embodiments of the present invention may include positioning of the sensor in a variety of suitable positions with respect to the permeable membrane. For instance, in one embodiment, the sensor may be mounted to the underside of an inflatable permeable membrane located above a sealing cuff. In further embodiments, the wall of the sealing cuff may be the permeable membrane, and the sensor may be mounted on the underside of the sealing cuff. Accordingly, the ETT may have a recess adapted to receive the sensor when the cuff is deflated. Still further, the sensor may be coupled to a diffusive band circumferentially disposed around the sealing cuff or may be integrated with a permeable membrane located on a distinct deployment cuff separate from the sealing cuff. Indeed, the sensor may be integrated with the permeable membrane in any of a variety of suitable ways such that the sensor may measure a presence or level of one or more gases and/or analytes in the trachea.

It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respirator arrest. For further example, the tracheal tubes may be coupled to an interface circuit and/or a monitor that is configured to receive data from the sensor, process such data, and display the processed data to an end user (e.g., medical technician, doctor, nurse, etc.).

Furthermore, although the embodiments of the present invention illustrated and described herein are discussed in the context of endotracheal tubes, it should be noted that presently contemplated embodiments may include a sensor disposed on a permeable membrane of any of a variety of suitable airway devices. For example, the sensor disposed on the permeable membrane may be coupled to a tracheostomy tube, a BronchoCath™ tube, a specialty tube, or any other airway device. Indeed, any device designed for use in an airway of a patient may be coupled to the sensor disposed on the permeable membrane. Furthermore, as used herein, the term "tracheal tube" may include an endotracheal tube, a tracheostomy tube, a BronchoCath™ tube, a specialty tube, or any other airway device.

Figures 1, 3, 4:
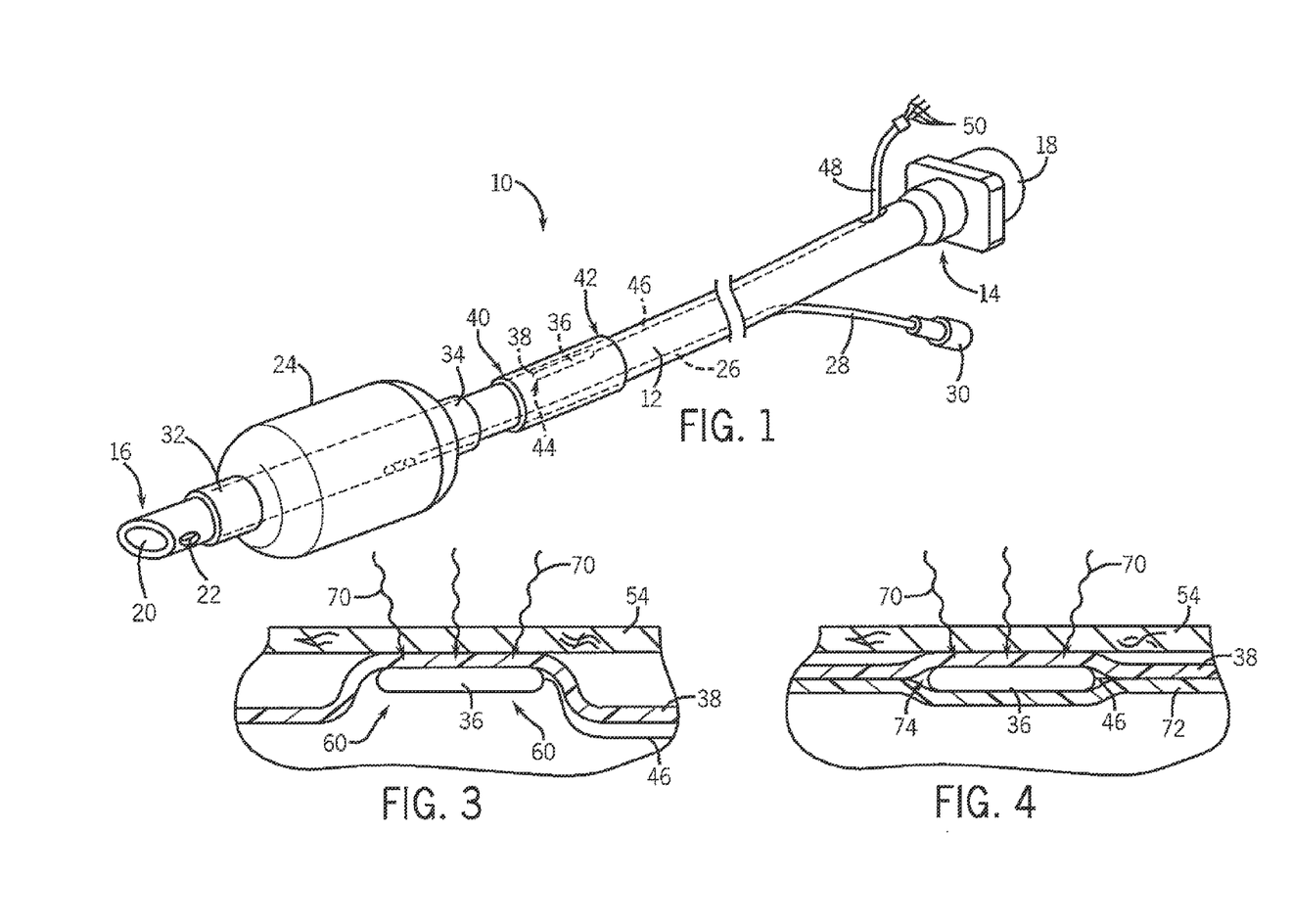
FIG. 1 is an elevational view of an exemplary endotracheal tube with a sensor disposed on an underside of a selectively permeable membrane in accordance with aspects of the present disclosure.
FIG. 3 illustrates an exemplary placement of a sensor on an underside of a permeable membrane in accordance with aspects of the present disclosure.
FIG. 4 illustrates an exemplary placement of a sensor between two permeable membranes in accordance with aspects of the present disclosure.

Turning now to the drawings, FIG. 1 is an elevational view of an exemplary endotracheal tube (ETT) assembly 10 in accordance with aspects of the present disclosure. The endotracheal tube 10 includes a central tubular body 12 with proximal and distal ends 14 and 16, respectively. In the illustrated embodiment, the proximal end 14 is outfitted with a connector 18 that may be attached to a mechanical ventilator during operation. The distal end 16 terminates in an opening 20 and may be placed in a trachea during operation to maintain airflow to and from a patient's lungs. A Murphy's eye 22 may be located on the tubular body 12 opposite the opening 20 to prevent airway occlusion when the tube assembly 10 is improperly placed within the trachea.

As illustrated, a cuff 24 configured to be inflated to seal against the walls of a body cavity (e.g., the trachea) may be attached near the distal end 16 of the tubular body 12, or along the body. The cuff 24 may be inflated via an inflation lumen 26 terminating in an inflation tube 28 connected to a fixture 30 located at the proximal end 14 of the tubular body 12. A first shoulder 32 and a second shoulder 34 of the cuff 24 secure the cuff 24 to the tubular body 12. In some embodiments, the first shoulder 32 and/or the second shoulder 34 may be folded up inside the cuff 24.

The tubular body 12 and the cuff 24 may be formed from materials having desirable mechanical properties (e.g., puncture resistance, pin hole resistance, tensile strength, and so forth) and desirable chemical properties (e.g., biocompatibility). In one embodiment, the walls of the cuff 24 may be made of a polyurethane (e.g., Dow Pellethane® 2363-80A) having suitable mechanical and chemical properties. In other embodiments, the walls of the cuff 24 may be made of a suitable PVC. In certain embodiments, the cuff 24 may be generally sized and shaped as a high volume, low pressure cuff that may be designed to be inflated to pressures between about 15 cm and 30 cm of water.

A sensor 36 is also coupled to the tubular body 12 and disposed behind a permeable membrane 38. The sensor 36 is configured to measure a presence or amount of at least one blood gas and/or blood analyte, such as carbon dioxide, oxygen, or pH, in the trachea during deployment. In the illustrated embodiment, the permeable membrane 38 is circumferentially coupled to the tubular body 12 at a first end 40 and a second end 42. During intubation and extubation, the sensor 36 may be disposed behind the permeable membrane 38 in a recess 44, as shown in FIG. 1. During measurement acquisition, however, the permeable membrane 38 is configured to expand via inflation, thus transporting the sensor 36 outward toward the tracheal wall where one or more blood gases and/or blood analytes may diffuse across the permeable membrane as described in more detail below. The permeable membrane 38 may be made of any suitable material, such as silicone, polyvinyl chloride (PVC), or polytetrafluoroethylene (Teflon).

The sensor 36 is connected to a dedicated lumen 46 terminating in a conduit 48 and one or more conductors 50. That is, one or more support cables and/or conductors may be positioned in the lumen 46 to facilitate a bidirectional exchange of data, power, and so forth between the sensor 36 and an external support system. For example, during or after intubation, the sensor 36 may be supplied with power and may export data via the lumen 46. In this way, the lumen 46 and the conduit 48 facilitate bidirectional communication between the sensor 36 located within the patient and the support system positioned outside the patient via the conductors.

Figure 2:
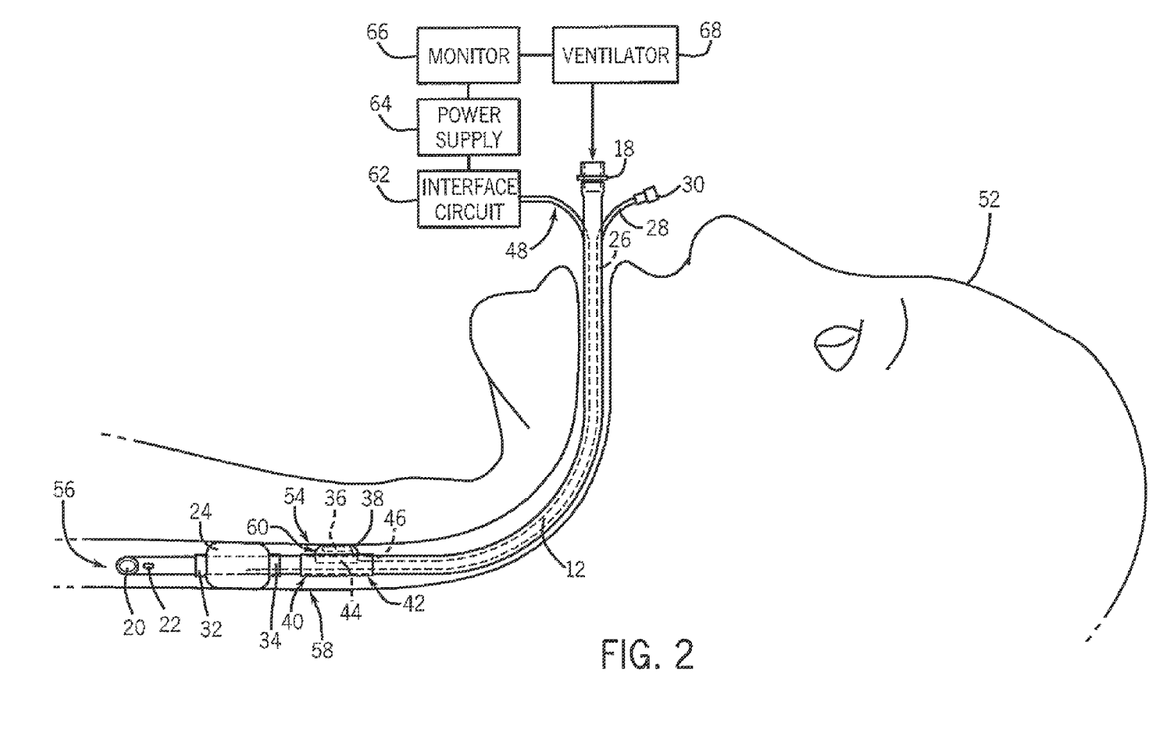
FIG. 2 illustrates the endotracheal tube of FIG. 1 positioned in a trachea of a patient lying in a semirecumbent position with a deployed sensor in accordance with aspects of the present disclosure.

FIG. 2 illustrates an exemplary system including a patient 52 intubated with the endotracheal tube assembly 10 of FIG. 1 in accordance with embodiments of the present invention. As illustrated, the patient 52 is shown lying in a semirecumbent position as may be typical during long term intubations. In the illustrated embodiment, the lumen 46 is positioned within the tubular body 12 such that the sensor 36 is deployable on the side of the cuff 24 that faces the ventral side of the patient during intubation in the semirecumbent position. That is, in the embodiment shown, the sensor 36 may be deployed to contact a first side or wall 54 of a trachea 56 of the patient. In some embodiments, this position may offer advantages over sensors configured to be deployed close to a second side or wall 58 of the trachea 56 since mucus may be prone to accumulating near the dorsal side of the patient during intubation in a semirecumbent position. In some embodiments, by deploying the sensor 36 near the ventral side of the patient, interference from accumulated secretions may be prevented and one or more suctioning ports may be included if desired. However, other embodiments may feature sensors 36 that are minimally affected or unaffected by secretion accumulation. In such embodiments, the sensor 36 may be placed in any desirable location around the circumference of the trachea.

During use, after intubation of the patient 52, the permeable membrane 38 is expanded via inflation, thus bringing the sensor 36, which is coupled to the membrane 38, in close proximity to the tracheal wall 54. The permeable membrane 38 may be inflated via any mechanism, such as by an inflation lumen extending from a location external to the patient, along the tubular body 12, and into the permeable membrane 38. The membrane 38 may be adapted to selectively allow passage of one or more analytes or gases while preventing passage of other gases and/or particles. For example, the membrane 38 may be selectively permeable to gases such as oxygen or carbon dioxide. During deployment of the sensor 36, the gases and analytes present in the tracheal mucosa may diffuse across the permeable membrane 38 and equilibrate with a cavity 60 formed when the membrane 38 is inflated. In this way, the sensor 36 may be configured to measure a presence or level of one or more gases and/or analytes in the tracheal mucosa without directly contacting the tracheal wall. Accordingly, the sensor 36 may be any suitable carbon dioxide, oxygen, pH, or other gas or analyte sensor, such as an electrochemical sensor, a fluorometric sensor, or a mid-infrared sensor. Furthermore, the sensor may be configured to simultaneously or sequentially measure more than one gas or analyte level.

After obtaining the desired measurements, the sensor 36 may be configured to return to the recess 44. For example, negative pressure may be applied to the cavity 60, thus forcing the inflated membrane 38 to deflate and the sensor 36 to collapse into recess 44. This feature may have the effect of facilitating removal of the tracheal tube assembly 10 from the patient 52 after intubation. Furthermore, the sensor 36 may be selectively deployed to obtain a measurement and subsequently returned to the predeployment position when desired by an operator. For example, the sensor 36 may be manually deployed or may be set to automatically deploy at predetermined time intervals.

The lumen 46 and the conduit 48 may couple one or more devices or systems to the sensor 36 during intubation. In the illustrated embodiment, the conduit 48 is communicatively coupled to an interface circuit 62 that is configured to receive and process measurement data acquired by the sensor 36. The interface circuit 62 is coupled to a power supply 64 that provides power for the sensor 36 and any electronics associated with the sensor 36. The interface circuit 62 may also facilitate the transfer of power to the sensor 36 in some embodiments. The power supply 64 is further coupled to a monitor 66 that is adapted to interpret and display the measurements received from the sensor 36 via the interface circuit 62. To that end, the monitor 66 may include a memory, a display, code configured to provide a specific output, and so forth. For example, the monitor 66 may include software adapted to integrate measurements taken at preset intervals over a predetermined period of time and/or to average or otherwise process measurements taken from multiple positions within the trachea 56. The monitor 66 may be connected to a ventilator 68 that supplies air to the patient 52 through connector 18. It should be noted that in further embodiments, the conduit 48 may be coupled to additional devices and systems not shown in FIG. 2. For example, the conduit 48 may be coupled to an inflation device and a computer that may facilitate a timed inflation and deflation of the membrane 38 as preprogrammed or desired by the operator. Indeed, the conduit 48 may be coupled to any suitable auxiliary device or system that is configured for use with a tracheal tube.

Still further, in other embodiments, the sensor 36 may be adapted to unidirectionally or bidirectionally communicate with one or more external devices via wireless communication. That is, in some embodiments, the sensor 36 may not be coupled to the external devices via the conductors. In such embodiments, the sensor 36 may wirelessly communicate with devices such as a monitor, mobile phone, PDA, or central communications point. Further embodiments may feature a single conductor that couples the sensor 36 to the power supply 64, while data communication occurs via a wireless route.

FIGS. 3 and 4 illustrate certain possible placements of the sensor 36 with respect to the membrane 38 and the tracheal wall 54 during deployment. Specifically, FIG. 3 illustrates an exemplary deployed sensor 36 coupled to the permeable membrane 38. In the illustrated embodiment, the membrane 38 abuts the tracheal wall 54 during deployment. Subsequently, one or more blood gases and/or blood analytes, as represented by arrows 70, diffuse from the tracheal mucosa through the tracheal wall 54 and the permeable membrane 38. In this way, the blood gases and/or blood analytes 70 equilibrate with the cavity 60 where the sensor 36 is located. The sensor 36 may then acquire measurements indicative of the presence or concentration of one or more gases or analytes in the tracheal mucosa.

Likewise, FIG. 4 is a schematic of an exemplary deployed sensor 36 located between the first permeable membrane 38 and a second permeable membrane 72. That is, in this embodiment, the sensor 36 may be embedded between two permeable membranes 38 and 72. As before, the gases and/or analytes 70 located in the tracheal mucosa diffuse through the tracheal wall 54 and the first permeable membrane 38 to equilibrate with a cavity 74 disposed between the first membrane 38 and the second membrane 72. In this way, the sensor 36 may measure a presence or level of one or more blood gases and/or analytes without directing contacting the tracheal wall 54.

Figure 5:
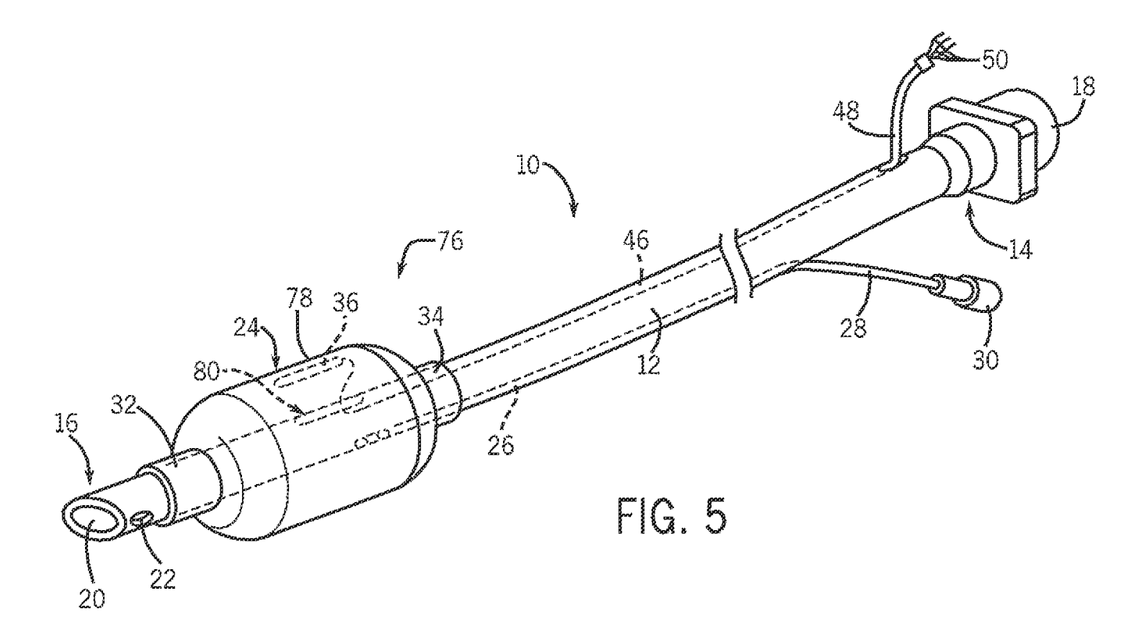
FIG. 5 is an elevational view of an exemplary endotracheal tube with a sensor located on an underside of an outer wall of a selectively permeable cuff in accordance with aspects of the present disclosure.

FIG. 5 is an elevational view of an EFT assembly 76 having the sensor 36 mounted on an underside of a wall 78 of the cuff 24 in accordance with embodiments of the present invention. As before, the sensor 36 is configured to measure the presence or level of one or more blood gases and/or blood analytes. However, in this embodiment, the wall 78 of the cuff 24 is adapted to selectively allow the desired gases and/or analytes to permeate, thus enabling the sensor 36 to acquire measurements without directly contacting the tracheal mucosa. The tubular body 12 includes a recess 80 that is configured to receive the sensor 36. That is, the sensor 36 may remain in the recess while the ETT assembly 76 is placed in and removed from the trachea. The sensor 36 is deployed as the cuff 24 is inflated via inflation lumen 26. In the illustrated embodiment, the sensor 36 remains deployed while the cuff 24 is inflated.

It should be noted that the wall 78 of the cuff 24 may be made of any material that is both permeable to the desired gases and analytes as well as able to seal against the tracheal walls. In the illustrated embodiment, the sensor 36 is mounted to the underside of the sealing cuff 24. However, in further embodiments, the sensor 36 may be mounted on the underside of an additional cuff with a selectively permeable wall. That is, the sealing cuff 24 may seal against the walls of the trachea to maintain the ETT assembly 76 in the desired position while the additional cuff may be adapted to deploy the sensor. Indeed, the sensor 36 may be located anywhere on the underside of the sealing cuff or anywhere on the underside of any suitable additional cuff.

Figure 6:
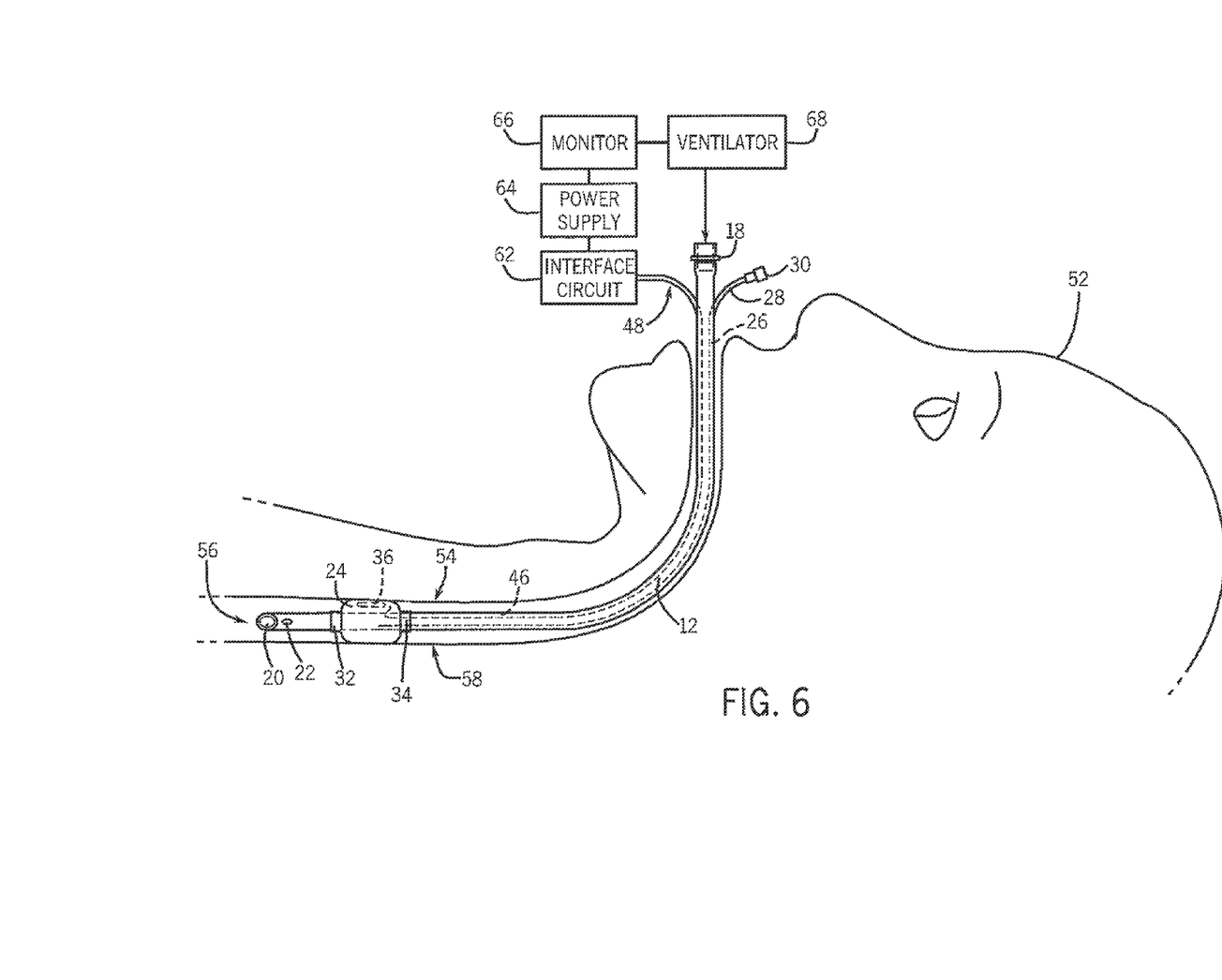
FIG. 6 illustrates the endotracheal tube of FIG. 5 positioned in a trachea of a patient lying in a semirecumbent position with a deployed sensor in accordance with aspects of the present disclosure.

FIG. 6 illustrates an exemplary system including a patient 52 intubated with the endotracheal tube assembly 76 of FIG. 5 in accordance with embodiments of the present invention. As illustrated, the patient 52 is shown lying in a semirecumbent position as may be typical during long term intubations. As before, in the illustrated embodiment, the lumen 46 is positioned within the tubular body 12 such that the sensor 36 is deployable on the side of the cuff 24 that faces the ventral side of the patient during intubation to minimize the potential effects of accumulated secretions on measurement acquisition. However, it should be noted that other embodiments may feature sensors 36 that are minimally affected or unaffected by secretion accumulation. In such embodiments, the sensor 36 may be placed in any desirable location around the circumference of the trachea.

The sensor 36 is illustrated in a deployed position mounted on the underside of the cuff wall 78. During use, the sensor 36 is configured to deploy from the recess 80 when the cuff 24 is inflated and return to the recess 80 when the cuff 24 is deflated. That is, negative pressure may be applied to the cuff 24 to force the sensor 36 back to its predeployment position. While deployed, the sensor 36 is adapted to measure the presence or level of one or more blood gases and/or blood analytes after diffusion from the tracheal wall and through the permeable membrane 78.

As before, the lumen 46 and the conduit 48 may couple one or more devices or systems to the sensor 36 during intubation. In the illustrated embodiment, the conduit 48 is coupled to the interface circuit 62 that is configured to receive and process measurement data acquired by the sensor 36. The interface circuit 62 is coupled to the power supply 64, which is further coupled to the monitor 66 that is adapted to interpret and display the measurements received from the sensor 36 via the interface circuit 62. The monitor 66 may be connected to the ventilator 68 that supplies air to the patient 52 through connector 18. Again, the conduit 48 may be coupled to additional devices and systems not shown in FIG. 6.

Figure 7:
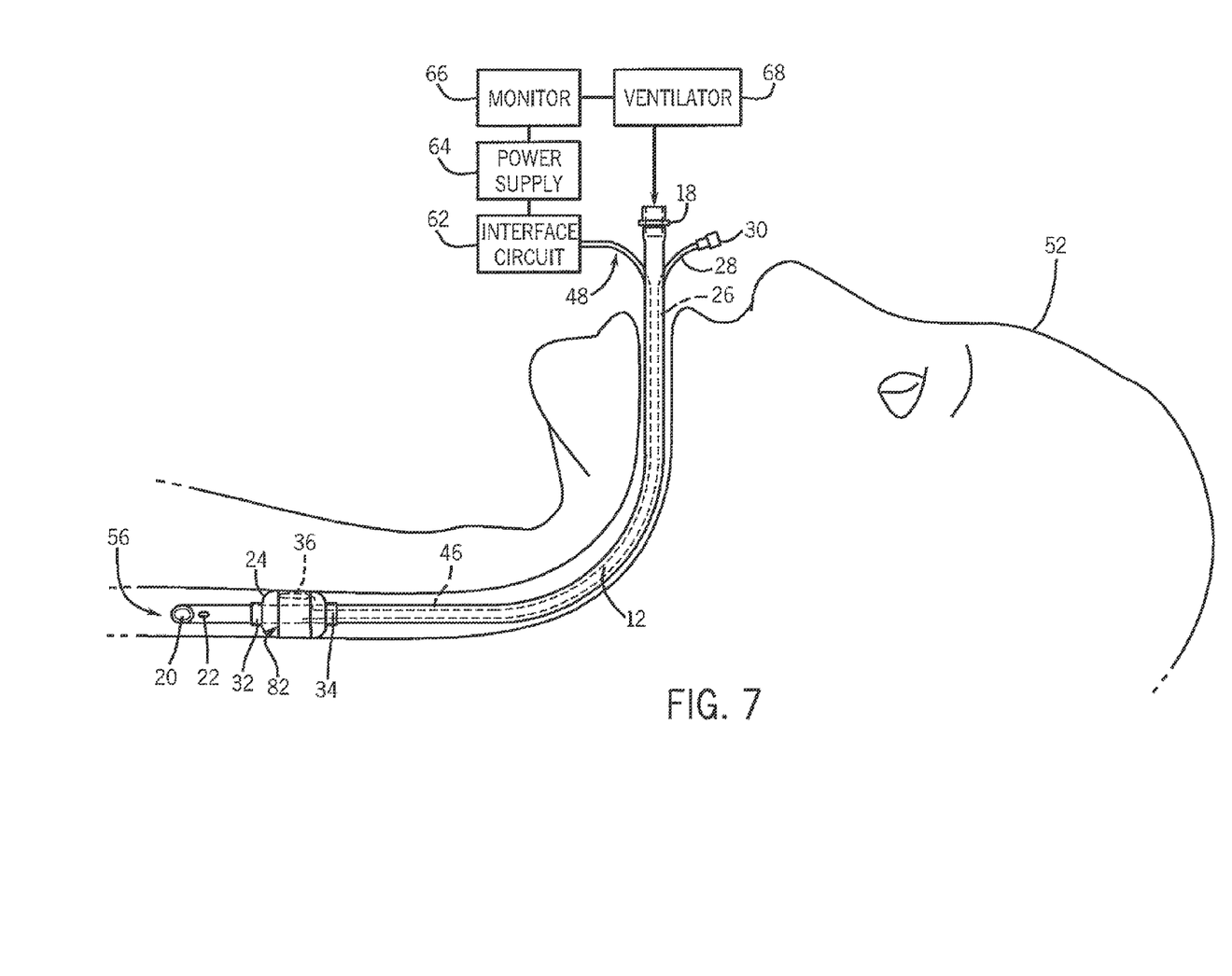
FIG. 7 illustrates a patient intubated with an exemplary endotracheal tube with a sensor disposed in a selectively permeable band circumferentially coupled to a cuff in accordance with aspects of the present disclosure.

FIG. 7 illustrates an exemplary system including the patient 52 lying in a semirecumbent position and intubated with an alternative embodiment of the ETT assembly. As shown, this embodiment includes the cuff 24 having the sensor 36 and a band 82 disposed thereon. The band 82 is circumferentially coupled to the cuff 24 around the radius of the trachea. Furthermore, the band 82 is a permeable membrane adapted to permit the selective diffusion of one or more gases or analytes from the tracheal mucosa. The sensor 36 is integral with the band 82 and the cuff 24 and is configured to sense the presence or level of one or more blood gases and/or blood analytes. Since the band 82 is disposed about the circumference of the trachea, such embodiments may enable the sensor 36 to acquire measurements indicative of the average concentrations of the gases and/or analytes from multiple radial locations around the trachea. That is, the band 82 may reduce the effect of local noise on the acquired measurements as compared to designs with a single sensor located in a predetermined position. As before, the sensor 36 may be coupled to a variety of external devices, such as the interface circuit 62, the power supply 64, the monitor 66, and the ventilator 68.

In one embodiment, the band 82 may be made of a diffusive material, such as silicone, that facilitates the diffusion of the blood gases and/or analytes throughout the band 82. That is, the gases and analytes present at all radial positions in the tracheal mucosa will first diffuse into the band 82 and then diffuse around the band 82 to form a uniform concentration throughout. The sensor 36 may then be integrated into the band 82 at any desirable radial position to acquire measurements. The data acquired from the location of the sensor 36 is indicative of the average level of gases or analytes in the diffusive band 82, which corresponds to the average level of gases or analytes in the tracheal mucosa. Still further, in other embodiments, multiple sensors 36 may be disposed at multiple positions throughout the band 82.

In further embodiments, the band 82 may be a circumferential cavity surrounded by a permeable membrane and filled with a fluid material suitable for sensing one or more blood gases and/or blood analytes. For example, in one embodiment, the band 82 may be a cavity filled with bicarbonate for sensing carbon dioxide. In this way, the band 82 may be the sensor in some embodiments. Still further, the band 82 may be a circumferential cavity surrounded by a permeable membrane, filled with a diffusive material, and interspersed with one or more sensors 36. For instance, sensors for a variety gases and analytes may be embedded in the diffusive material in a variety of radial locations throughout the band 82.

Figure 8:
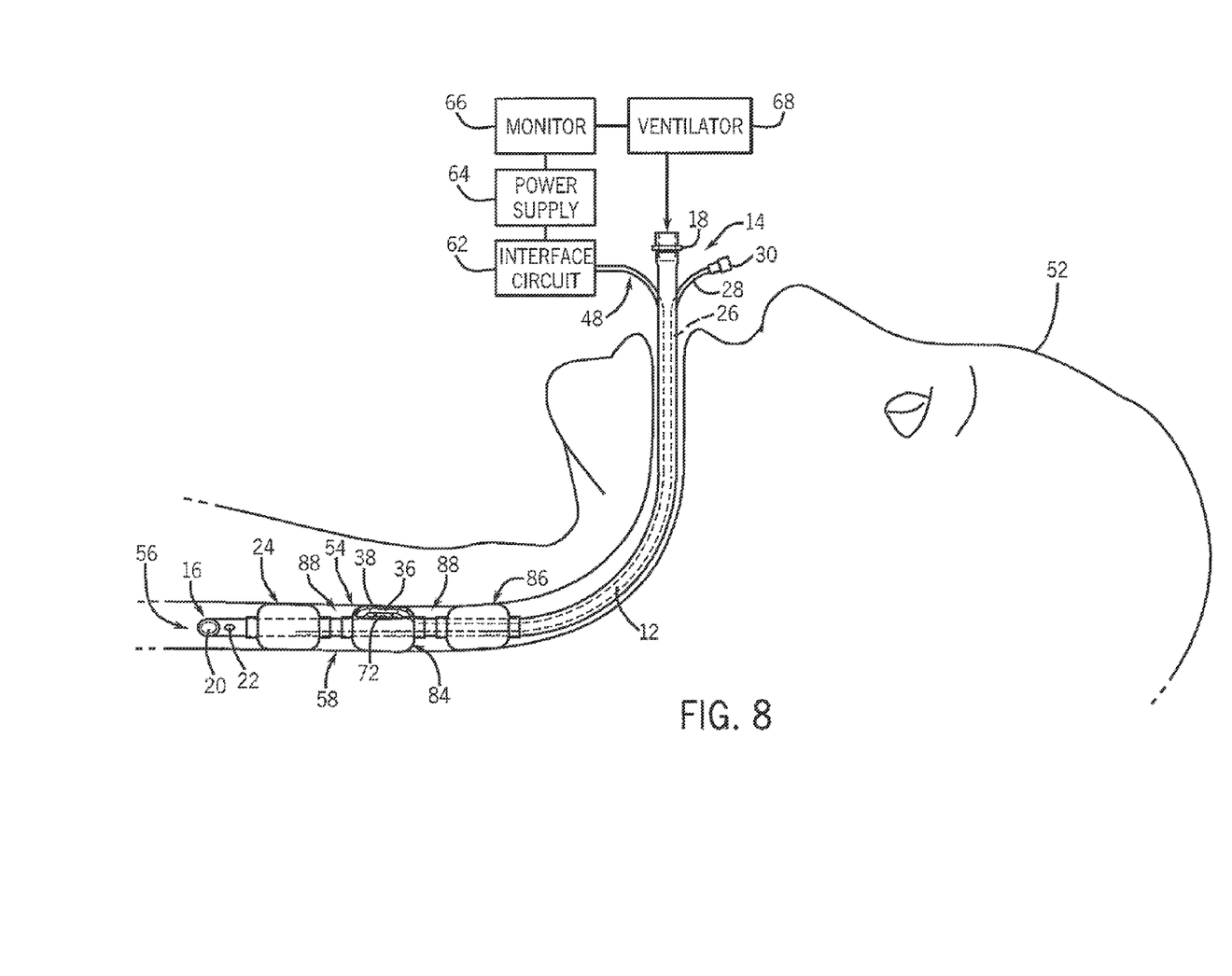
FIG. 8 illustrates a patient intubated with an exemplary endotracheal tube with a sensor disposed on an underside of a wall of a deployment cuff in accordance with aspects of the present disclosure.

FIG. 8 illustrates an exemplary system including the patient 52 lying in a semirecumbent position and intubated with an alternative embodiment of the ETT assembly. In this embodiment, the ETT assembly includes the sealing cuff 24 that seals against the walls of the trachea 54 and 58, a deployment cuff 84 that deploys the sensor 36, and a second sealing cuff 86 that seals against the walls of the trachea 54 and 58. The first sealing cuff 24 is attached to the tubular body 12 above the Murphy's eye 22 toward the distal end 16 of the ETT assembly. The second sealing cuff 86 is attached to the tubular body 12 below the connector 18 toward the proximal end 14 of the ETT assembly. The deployment cuff 84 is disposed on the body 12 at a location between the first sealing cuff 24 and the second sealing cuff 86. When the sealing cuffs 24 and 86 are inflated, a cavity 88 is defined by the area between the first sealing cuff 24, the second sealing cuff 86, and the tracheal walls 54 and 58. Isolation of the cavity 88 may facilitate the acquisition of measurements by the sensor 36 because the blood gases and/or blood analytes may equilibrate between the mucosa and the isolated cavity, thus ensuring that the acquired measurements are indicative only of gas parameters in the mucosa and not end tidal movement in the air. It should be noted that in additional embodiments, the deployment cuff 84 may be replaced with the sensor 36 mounted under an inflatable permeable membrane. In such embodiments, the sealing cuff 86 may facilitate the alignment of the tracheal tube when the sensor 36 is deployed. Additionally, the sensor 36 may be deployed against the tracheal wall in the isolated cavity.

As shown, the sensor 36 is embedded between the first membrane 38 and the second membrane 72 of the deployment cuff 84, as described in detail above with respect to FIG. 3. When inflated, the deployment cuff 84 is adapted to deploy the sensor 36 in the cavity 88 such that the sensor may acquire measurements. To that end, the membranes 38 and 72 may be permeable to one or more blood gases and/or blood analytes. After the concentration of the gases and/or analytes in the tracheal mucosa equilibrate with those in the cavity 88, measurements taken in the cavity 88 are reflective of the concentrations of the gases and analytes in the mucosa. After measurement acquisition, the deployment cuff 84 is configured to deflate as desired by an operator.

It should also be noted that the cuffs with the sensors disposed behind permeable membranes, as shown in the embodiments of FIGS. 5, 6, and 7, may be coupled to a tracheal tube body as shown in FIG. 8. That is, the cuffs of FIGS. 5, 6, and 7 may be the deployment cuff 84 of FIG. 8. In such embodiments, the cuffs of FIGS. 5, 6, and 7 may deploy the sensor in a cavity defined by the area between the first sealing cuff 24 and the second sealing cuff 86. As before, the sensors 36 may be adapted to measure the presence or level of one or more blood gases and/or blood analytes in the trachea.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube system, comprising: a tubular body comprising an open distal end for ventilating a patient; a cuff disposed around the tubular body above the open distal end and comprising an integral membrane that is selectively permeable to a blood gas and/or blood analyte; a sensor disposed on an underside of a wall of the cuff and configured to measure a level of the blood gas and/or the blood analyte in the trachea when the cuff is inflated; and a recess disposed in the tubular body, wherein the recess receives the sensor when the cuff is deflated.

2. The tracheal tube system of claim 1, wherein the cuff is configured to be inflated to seal the cuff against a wall of a trachea and to be deflated via the application of negative pressure.

3. The tracheal tube system of claim 2, wherein the sensor is configured to collapse into the recess when the negative pressure is applied to the cuff.

4. The tracheal tube system of claim 1, wherein the sensor comprises bicarbonate for sensing a presence or level of carbon dioxide.

5. The tracheal tube system of claim 1, comprising a connector configured to be received on a proximal end of the tubular body to couple the tubular body to a mechanical ventilator.

6. The tracheal tube system of claim 5, wherein the membrane comprises at least one of silicone, polyvinyl chloride, or polytetrafluoroethylene.

7. The tracheal tube system of claim 5, comprising a ventilator configured to supply air to the patient via the tubular body.

8. The tracheal tube system of claim 5, comprising a monitor communicatively coupled to the sensor and configured to receive one or more measurements from the sensor and to interpret and/or display the received one or more measurements.

9. The tracheal tube system of claim 5, wherein the blood gas and/or blood analyte comprises carbon dioxide, oxygen, pH, or a combination thereof.

10. The tracheal tube system of claim 1, wherein the cuff comprises first and second shoulders configured to couple the cuff to the tubular body.

11. The tracheal tube system of claim 1, wherein the distal end of the tubular body comprises a Murphy's eye.

12. A tracheal tube system, comprising: a tubular body comprising an open distal end for ventilating a patient and a recess disposed therein; a cuff disposed around the tubular body above the open distal end and comprising a membrane that is selectively permeable to a blood gas and/or blood analyte; and a sensor coupled to the membrane and configured to measure a level of the blood gas and/or the blood analyte in the trachea, wherein the recess receives the sensor during intubation and extubation.

13. A tracheal tube system, comprising: a tubular body comprising an open distal end for ventilating a patient and a recess disposed therein; a cuff disposed around the tubular body above the open distal end and comprising a membrane that is selectively permeable to a blood gas and/or blood analyte; and a sensor disposed behind the membrane and coupled to the cuff, wherein the sensor is configured to be deployed to measure a level of the blood gas and/or the blood analyte in the trachea when the cuff is inflated, and wherein the recess receives the sensor when the cuff is deflated.

14. The tracheal tube system of claim 13, wherein the blood gas and/or blood analyte comprises carbon dioxide, oxygen, pH, or a combination thereof.

15. The tracheal tube system of claim 13, comprising a connector configured to be received on a proximal end of the tubular body to couple the tubular body to a mechanical ventilator.

* * * * *